(12) United States Patent
Toshimitsu et al.

(10) Patent No.: US 9,370,495 B2
(45) Date of Patent: Jun. 21, 2016

(54) ADHESIVE PATCH

(75) Inventors: Arata Toshimitsu, Tsubuka (JP); Naoko Fujita, Tsubuka (JP)

(73) Assignee: HISAMITSU PHARMACEUTICAL CO., INC., Toshu-Shi, Saga (JP)

( * ) Notice: Subject to any disclaimer, the term of this patent is extended or adjusted under 35 U.S.C. 154(b) by 0 days.

(21) Appl. No.: 13/580,332

(22) PCT Filed: Feb. 24, 2011

(86) PCT No.: PCT/JP2011/054143
§ 371 (c)(1),
(2), (4) Date: Aug. 21, 2012

(87) PCT Pub. No.: WO2011/105486
PCT Pub. Date: Sep. 1, 2011

(65) Prior Publication Data
US 2012/0321690 A1    Dec. 20, 2012

(30) Foreign Application Priority Data
Feb. 24, 2010    (JP) ................ P2010-039312

(51) Int. Cl.
*A61F 13/02*    (2006.01)
*A61K 9/70*    (2006.01)
*A61K 31/18*    (2006.01)

(52) U.S. Cl.
CPC ............... *A61K 9/7053* (2013.01); *A61K 31/18* (2013.01)

(58) Field of Classification Search
CPC ..................... A61K 9/7053; A61K 31/18
See application file for complete search history.

(56) References Cited

U.S. PATENT DOCUMENTS

2008/0226697 A1*   9/2008   Yamaguchi et al. .......... 424/448
2011/0028880 A1*   2/2011   Uchida et al. .................. 602/48

FOREIGN PATENT DOCUMENTS

| JP | S57176908 A | 10/1982 | |
| JP | S58-65168 | 4/1983 | |
| JP | 62-51933 B2 | 11/1987 | |
| JP | 63-20410 B2 | 4/1988 | |
| JP | 64-71811 A | 3/1989 | |
| JP | 3-173816 A | 7/1991 | |
| JP | 8-92080 A | 4/1996 | |
| JP | 2007016020 A | 1/2007 | |
| KR | 1020087025669 | * 12/2013 | ............... C09J 11/04 |
| WO | 2005/102393 A1 | 11/2005 | |
| WO | 2007/023791 A1 | 3/2007 | |
| WO | 2007/126067 A1 | 11/2007 | |
| WO | WO 2007126067 A1 * | 11/2007 | ............ C09J 201/00 |
| WO | 2009107476 A1 | 9/2009 | |

OTHER PUBLICATIONS

International Preliminary Report on Patentability for International Patent Application No. PCT/JP2011/054143; mailed on Sep. 27, 2012.
Office Action issued in Japanese Patent Application No. P2012-501843 dated Feb. 25, 2014, two (2) pages.

* cited by examiner

*Primary Examiner* — Nannette Holloman
(74) *Attorney, Agent, or Firm* — Nath, Goldberg & Meyer; Joshua B. Goldberg; Scott H. Blackman

(57) ABSTRACT

The present invention provides a patch having a backing and a pressure-sensitive adhesive layer on the backing, wherein the pressure-sensitive adhesive layer contains a pressure-sensitive adhesive base composed of a polymer having a hydroxyl group, a drug, polyvinylpyrrolidone and a multivalent metal chloride.

5 Claims, 1 Drawing Sheet

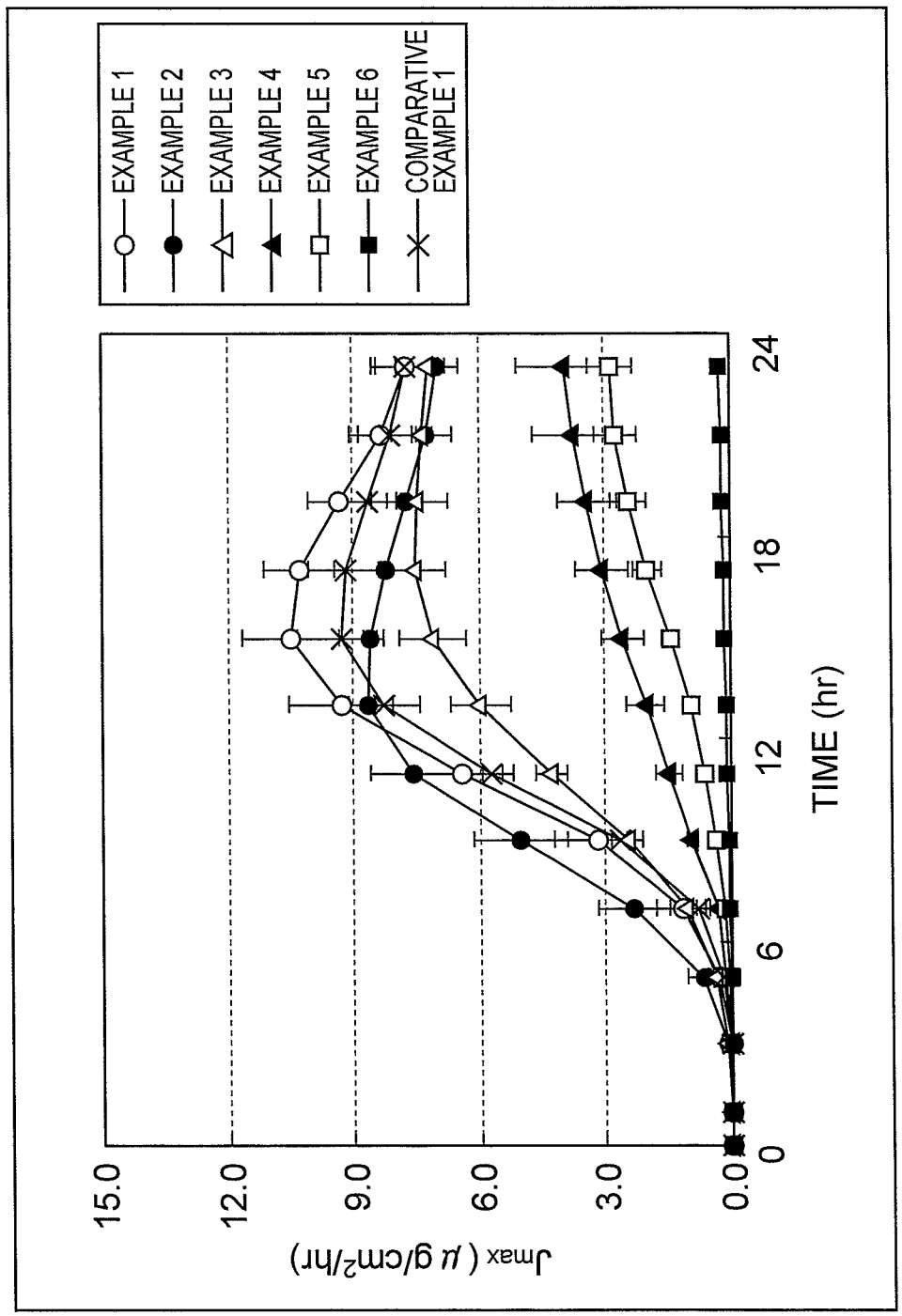

ADHESIVE PATCH

TECHNICAL FIELD

The present invention relates to a patch.

BACKGROUND ART

A patch is a preparation which is applied to the skin, or the like, for a predetermined period of time and allows a drug to be absorbed directly from the application surface for treatment. To allow drug efficacy to work faster and continuously when a drug is applied transdermally, it is required to enhance the transdermal absorption of the drug. However, since the skin works as a barrier against invaders from the environment, a drug is hardly absorbed from the skin. Thus, for the purpose of enhancing the transdermal absorbability of a drug contained in a patch, studies have been conducted on various drugs (Patent Literatures 1 to 6).

CITATION LIST

Patent Literature

Patent Literature 1: Domestic re-publication of PCT international application WO07/023,791
Patent Literature 2: Domestic re-publication of PCT international application WO05/102393
Patent Literature 3: Japanese Examined Patent Publication No. 63-20410
Patent Literature 4: Japanese Examined Patent Publication No. 62-51933
Patent Literature 5: Japanese Patent Application Laid-Open No. 3-173816
Patent Literature 6: Japanese Patent Application Laid-Open No. 8-92080

SUMMARY OF INVENTION

Technical Problem

Even if the transdermal absorbability of a drug can temporarily be enhanced, however, a drug may be decomposed while a patch is stored or a drug and a pressure-sensitive adhesive base may bond to each other in a pressure-sensitive adhesive layer composing a patch, reducing a drug content in the patch, whereby consequently the drug content to be transdermally absorbed may sometimes be reduced.

Thus, an object of the present invention is to provide a patch with good drug content stability even after stored for a certain period of time.

Solution to Problem

The present invention provides a patch comprising a backing and a pressure-sensitive adhesive layer on the backing, wherein the pressure-sensitive adhesive layer contains a pressure-sensitive adhesive base composed of a polymer having a hydroxyl group, a drug, polyvinylpyrrolidone and a multivalent metal chloride. The —OH group in a carboxyl group is not considered as the hydroxyl group.

According to the present invention, the drug content is stabilized even after the patch is stored for a certain period of time when the pressure-sensitive adhesive layer containing a pressure-sensitive adhesive base and a drug further contains polyvinylpyrrolidone and a multivalent metal chloride. The reason why such an effect is rendered is not clearly known, but one of the reasons is assumed that the drug and the multivalent metal chloride form a complex, which is stabilized by polyvinylpyrrolidone.

It is preferable that the drug be at least one selected from the group consisting of basic drugs and pharmaceutically acceptable salts thereof. Further, it is preferable that the drug be at least one selected from the group consisting of tamsulosin and pharmaceutically acceptable salts thereof. When the drug is tamsulosin or a pharmaceutically acceptable salt thereof, the drug content stability is significantly improved and further the transdermal absorbability of the drug is also improved. Also, it is preferable that the multivalent metal chloride be aluminum chloride. When the multivalent metal chloride is aluminum chloride, the drug content stability is further improved.

It is preferable that the content of polyvinylpyrrolidone be 1 to 20% by mass based on the total mass of the pressure-sensitive adhesive layer. When the content of polyvinylpyrrolidone is adjusted to be within this range, the stability of transdermal absorbability of the drug is improved.

It is preferable that the content of multivalent metal chloride be 0.1 to 5.0% by mass based on the total mass of the pressure-sensitive adhesive layer. When the content of multivalent metal chloride is adjusted to be within this range, the drug content stability is further improved.

Also, it is preferable that the ratio by mass of multivalent metal chloride to the drug be 1:100 to 2:1. When the multivalent metal chloride and the drug are contained within such a ratio, the drug content is further stabilized over an extended period of time and the transdermal absorbability can be improved.

Advantageous Effects of Invention

According to the present invention, a patch with good drug content stability even after stored for a certain period of time, can be provided.

BRIEF DESCRIPTION OF DRAWING

FIG. 1 is a graph showing the drug transdermal absorbability of the patches prepared in Examples 1 to 6 and Comparative Example 1.

DESCRIPTION OF EMBODIMENTS

Hereinafter, preferred embodiments of the patch according to the present invention are described in detail. In the present specification, "%" refers to "% by mass" unless otherwise specified.

The patch of the embodiment is provided with a pressure-sensitive adhesive layer on a backing, and the pressure-sensitive adhesive layer may be formed on both surfaces or one surface of the principal surface of the backing. The pressure-sensitive adhesive layer contains at least a pressure-sensitive adhesive base composed of a polymer having a hydroxyl group, a drug, polyvinylpyrrolidone and a multivalent metal chloride.

For the polymer containing a hydroxyl group used as the pressure-sensitive adhesive base, vinyl polymers having a hydroxyl group are preferred, and for such a vinyl polymer, (meth)acrylate polymers having a hydroxyl group, vinyl acetate polymers having a hydroxyl group, and the like, are preferred.

For the (meth)acrylate polymer having a hydroxyl group, the copolymer having the first monomer unit derived from acrylate and/or methacrylate having no hydroxyl group and the second monomer unit derived from a monomer having a hydroxyl group is preferred. Also, the copolymer may further have the third monomer unit derived from a third monomer to adjust pressure-sensitive adhesive properties, and the like.

Preferred examples of the above acrylate and methacrylate having no hydroxyl group include acrylic acid or methacrylic acid linear alkyl esters such as methyl ester, ethyl ester, propyl ester, butyl ester, pentyl ester, hexyl ester, heptyl ester, octyl ester, nonyl ester, decyl ester, undecyl ester, dodecyl ester, and tridecyl ester; branched alkyl esters such as 2-ethyl hexyl ester.

It is preferable that the content of the first monomer unit in the (meth)acrylate polymer having a hydroxyl group be 30 to 99% by mol on a total amount basis of the monomer units consisting the (meth)acrylate polymer.

Also, the content of first monomer unit in the (meth)acrylate polymer having a hydroxyl group is preferably 40 to 90% by mass, more preferably 50 to 80% by mass, based on the total mass of the (meth)acrylate polymer.

Preferred examples of the monomer having a hydroxyl group include acrylates such as 2-hydroxyethyl acrylate, 3-hydroxypropyl acrylate, and 4-hydroxybutyl acrylate; methacrylates such as 2-hydroxyethyl methacrylate, 3-hydroxypropyl methacrylate, and 4-hydroxybutyl methacrylate; vinyl alcohols; allyl alcohols; 3-buten-1-ol; 3-buten-2-ol; etc.

It is preferable that the content of second monomer unit in the (meth)acrylate polymer having a hydroxyl group be 1 to 15% by mol on a total amount basis of the monomer units consisting the (meth)acrylate polymer.

Also, the content of second monomer unit in the (meth)acrylate polymer having a hydroxyl group is preferably 1 to 15% by mass, more preferably 2 to 10% by mass, based on the total mass of the (meth)acrylate polymer.

Examples of the third monomer include vinyl acetate, vinyl propionate, allylamine, styrene, vinyl pyrrolidone, methylvinyl pyrrolidone, vinylpyridine, vinyl piperidone, vinylpiperazine, vinyl pyrazine, acrylamide, and the like.

The (meth)acrylate polymer having a hydroxyl group may have a monomer unit derived from monomers having a carboxyl group such as acrylic acid and methacrylic acid, but it is preferable that the content of the monomer unit be 5% by mass or less based on the total mass of the (meth)acrylate polymer. When the content of monomer unit having a carboxyl group is adjusted to be within the above range, the drug release from the pressure-sensitive adhesive layer is likely to be good.

When a commercial adhesive is used to be the pressure-sensitive adhesive base composed of the polymer having a hydroxyl group, it is preferred to use a product which does not contain a crosslinking agent. Examples of such an adhesive include Duro-Tak 87-2287, Duro-Tak 87-2510, Duro-Tak 87-4287, Duro-Tak 87-208A (products of Henkel Japan Ltd.), and the like.

It is preferable that the content of the pressure-sensitive adhesive base composed of the polymer having a hydroxyl group be 25% by mass or more based on the total mass of the pressure-sensitive adhesive layer. When the content of adhesive base composed of the polymer having a hydroxyl group is adjusted to be within the above range, the cohesive force of the pressure-sensitive adhesive layer tends to be even further enhanced.

In addition to the pressure-sensitive adhesive base composed of the polymer having a hydroxyl group, an additional adhesive base may be contained to adjust the pressure-sensitive adhesive properties of the pressure-sensitive adhesive layer and the transdermal absorbability of the drug. For the additional adhesive base, it is preferred to use a polymer which does not have a group which dissociates the electric charge paired with the electric charge dissociated by the drug, in view of the transdermal absorbability of the drug. Specific examples include nonionic dissociative polymers such as vinyl acetate copolymers including vinylpyrrolidone copolymers; polyisobutylene; polyisoprene; vinyl acetate copolymers such as polyvinyl acetate, ethylene-vinyl acetate copolymers; styrene-butadiene-styrene block copolymers; styrene-isoprene-styrene block copolymers; and styrene-butadiene rubbers. It is preferable that the content of the additional adhesive base be 60% by mass or less based on the total mass of the pressure-sensitive adhesive layer to inhibit the reduction in the cohesive force of the pressure-sensitive adhesive layer.

The drug to be used in the present invention is not particularly limited insofar as it exhibits the drug efficacy when transdermally absorbed, and may be those used in various purposes such as agents for peripheral nerve, agents for sympathetic, agents for parasympathetic, agents for autonomic ganglion, agents for sensory nerve, systemic anesthetics, sedatives, antidementia drugs, anesthetics, pain relievers, analgesic and anti-inflammatory drugs, steroid hormones, stimulant drugs, drugs for psychotic nerve, local anesthetics, skeletal muscle relaxants, autonomic agents, anti-allergy agents, anti-histamine agents, cardiac stimulants, antiarrhythmic agents, diuretics, hypotensive agents, vasoconstrictors, vasodilators, calcium antagonist agents, antibacterial agents, agents for parasitic skin diseases, dermalaxia, antibiotics, antidotes, cough medicines, antipruritic drugs, sleeping drugs, antiasthmatic agents, hormone secretagogues, antiulcer drugs, anticancer drugs, vitamins, cholinergic drug, acetylcholinesterase inhibitors, estrogen, progesterone, antifungal drug, anti-Parkinson's disease drugs, antiemetic drug, and psychotropic drug.

Specific examples of such a drug include therapeutic drugs for dysuria such as tamsulosin and oxybutynin, β blocking drugs such as propranolol, pindolol, metoprolol, bisoprolol and labetalol, α blocking drugs such as prazosin, terazosin and doxazosin, β stimulants such as tulobuterol and the pharmaceutically acceptable salts thereof. Among these drugs, it is preferred to use a basic drug because a basic drug stably forms a complex with a multivalent metal chloride, significantly improving the drug content stability, and it is preferred to use tamsulosin and a pharmaceutically acceptable salt thereof because the transdermal absorbability is further improved.

Examples of the pharmaceutically acceptable salts of the drug include acid salts such as hydrochloride, nitrate, acetate, succinate, fumarate, tartrate, salicylate, sulfate and phosphate, of the drug, and it is preferred to use hydrochloride among these because the drug is further stabilized. Tamsulosin hydrochloride is an α1 receptor blocking agent and a therapeutic drug for dysuria associated with prostatomegaly.

The drug may be used singly or two or more may be used in combination, and may be used in the form of either inorganic salt or organic salt. Also, in consideration of the transdermal absorbability, the drug having a molecular weight of 600 or less is suitable.

It is preferable that the drug be added, in consideration of sufficient permeation amount of the patch and the like, within the range of 1 to 30% by mass based on the total mass of the pressure-sensitive adhesive layer. When an application for about 24 hours is considered, it is more preferred to add the drug in an amount of 1 to 15% by mass so that the drug added is not wasted. The most effective amount to be added is 1 to 10% by mass.

It is preferred to suitably select the drug and the pressure-sensitive adhesive base in consideration of the combination of the chemical structure of the drug and the functional group the pressure-sensitive adhesive base has. Given that the pressure-sensitive adhesive base has a carboxyl group and the drug is an amine drug, the transdermal absorbability of the drug tends to be reduced. This is presumably because the carboxyl group of the pressure-sensitive adhesive base and the amino group of the drug are ionically bonded, whereby the drug diffusion in the pressure-sensitive adhesive layer is inhibited. Accordingly, it is preferable that the combination of drug and adhesive base which does not form an ionic bond be selected. More specifically, when the drug is a basic drug having a basic dissociative group, the pressure-sensitive adhesive base may be nonionic dissociative or may have a basic dissociative group. When the drug is an acidic drug having an acidic dissociative group, the pressure-sensitive adhesive base may be nonionic dissociative or may have an acidic dissociative group. When the drug is nonionic dissociative, the pressure-sensitive adhesive base may be nonionic dissociative or may have an acidic or basic dissociative group. Examples of the above acidic dissociative group include a carboxyl group, a sulfonic acid group, and the like, and examples of the basic dissociative group include a primary amino group, a secondary amino group, a tertiary amino group, a quaternary ammonium group, and the like.

The pressure-sensitive adhesive layer contains polyvinylpyrrolidone. To enhance the drug transdermal absorbability and the stability of adhesive layer, the polyvinylpyrrolidone is contained, based on the total mass of the pressure-sensitive adhesive layer, preferably 1 to 20% by mass, more preferably 1 to 10% by mass, further preferably 1 to 6% by mass. Also, the content ratio by mass of the drug to polyvinylpyrrolidone is preferably 10:1 to 1:3, more preferably 2:1 to 1:2.

For the multivalent metal chloride, multivalent metal chlorides in which the metal is bivalent or trivalent are preferred, and examples of such a multivalent metal chloride include magnesium chloride, calcium chloride, zinc chloride, stannous chloride, ferric chloride, aluminum chloride, and the like, with aluminum chloride in which the metal is trivalent aluminum being particularly preferred. The amount of multivalent metal chloride to be added is not limited insofar as the amount is within the range wherein the stabilizing effect on the drug (content stabilizing effect) is rendered, but is typically added in the range from 0.1 to 5.0% by mass in a total mass basis of the pressure-sensitive adhesive layer. The amount to be added within this range can exhibit a stabilizing effect without largely affecting the preparation properties and the transdermal absorbability. This range is preferably 0.2 to 3.0% by mass, further preferably 0.1 to 1.0% by mass. To further enhance the drug content stability over an extended period of time, the content ratio by mass of the multivalent metal chloride to the drug is preferably 1:100 to 2:1, more preferably 1:50 to 1:1. The content ratio by mass of the multivalent metal chloride to the pressure-sensitive adhesive base composed of the polymer having a hydroxyl group, in consideration of the stability of adhesive layer, is preferably 1:1000 to 1:100, more preferably 1:900 to 1:50. Further, the content by mass of multivalent metal chloride to polyvinylpyrrolidone, to achieve good drug stability and transdermal absorbability, is preferably 1:5 to 1:50, more preferably 1:5 to 1:30.

The patch of the present invention can further contain silicic acid in the pressure-sensitive adhesive layer to enhance the drug transdermal absorbability as well as firmness and cohesive force of the pressure-sensitive adhesive layer. Examples of the silicic acid include silica gel produced from sodium silicate, colloidal silica (dispersion) which is a microparticle of silicic anhydride produced from water glass, microparticulate silicic anhydride produced from a chlorinated product of ferric silicon in the gaseous phase (light anhydrous silicic acid), etc. Among these, silicic anhydride is more preferred than hydrous silicate, with light anhydrous silicic acid being more preferred.

When the silicic acid is particulate, the particle diameter of silicic acid particle is preferably an average particle diameter of 50 µm or less, particularly preferably 16 µm or less. Within the above range, nonuniform coating is unlikely to be caused at the time of preparing the pressure-sensitive adhesive layer. Also, when the particle diameter is made smaller and the surface area is made larger, the transdermal absorbability of the drug is enhanced and further the firmness and the cohesive force of the pressure-sensitive adhesive layer are likely to be enhanced.

Furthermore, when a silicic anhydride particle is used to be the silicic acid particle, it is preferred to use a particle which has the hydrophilic surface, in the light of transdermal absorbability of the drug and also due to the good miscibility with medium (solvent) at the time of preparing the pressure-sensitive adhesive layer.

It is preferable that the amount of silicic acid to be added be in the range of 0.2 to 10% by mass based on the total mass of the pressure-sensitive adhesive layer. Within the above range, the flowability of liquid to be coated at the time of preparing the pressure-sensitive adhesive layer is good, whereby the pressure-sensitive adhesive layer of a uniform thickness can be obtained. The specific surface area of silicic acid particle is, in view of enhancing the firmness of adhesive layer, preferably 100 $cm^2/g$ or more, more preferably 300 $cm^2/g$ or more. For the silicic acid particle, light anhydrous silicic acid particles having, for example, a particle diameter of 7 to 16 µm are commercially available and can be desirably used.

The patch of the present invention, to enhance the transdermal absorbability of the drug, can further contain an absorption promoting agent in the pressure-sensitive adhesive layer. Such an absorption promoting agent is not limited and can be suitably selected from known absorption promoting agents. Specific examples include fatty acid esters such as lower alcohols, saturated or unsaturated linear or branched aliphatic alcohols, saturated or unsaturated aliphatic ethers, saturated or unsaturated fatty acids, fatty acid salts, sorbitan fatty acid esters and fatty acid glycerol esters, vegetable oils and fats such as fatty acid amides, terpenes and olive oils, animal oils and fats such as squalene, N-methylpyrrolidone, crotamiton, azacycloalkane derivatives, and the like.

Examples of the saturated or unsaturated fatty acid include fatty acids such as organic acids having 2 to 4 carbon atoms including acetic acid, propionic acid, butyric acid, lactic acid, glycolic acid, malic acid, tartaric acid and citric acid; linear or branched chain saturated fatty acids having 6 to 18 carbon atoms including caproic acid, caprylic acid, capric acid, lauric acid, myristic acid, palmitic acid, stearic acid, isostearic acid, linolic acid and linolenic acid; unsaturated fatty acids such as oleic acid, linolic acid and linolenic acid; with acetic acid, capric acid, lauric acid, and the like, being preferably used. Examples of the fatty acid salt include potassium salt, sodium salt, calcium salt, magnesium salt, and the like, of the fatty acids described above, with sodium acetate, sodium caprate, sodium laurate, and the like, being preferably used, and sodium acetate being particularly preferably used. Examples of the fatty acid ester include esters of alcohols and the fatty acids described above, and examples of the alcohol include aliphatic alcohols such as methanol, ethanol, propanol and isostearyl alcohol; polyvalent alcohols such as ethylene glycol, propylene glycol, glycerol and polyethylene glycol; sugar alcohols such as sorbitol; etc. Examples of the fatty acid ester include isopropyl myristate, isopropyl palmitate, sorbitan monooleate, sorbitan monolaurate, and the like. Example of the fatty acid amide include amides of the fatty acids described above and amines such as diethanolamine, with lauric acid diethanol amide, and the like, being preferably used.

The content of absorption promoting agent ranges, to enhance the transdermal absorbability of the drug, preferably 1 to 30% by mass, more preferably 1 to 10% by mass, further preferably 1 to 6% by mass, based on the total mass of the pressure-sensitive adhesive layer. The content number of mole of the absorption promoting agent is, to enhance the transdermal absorbability of the drug, preferably 0.5 to 5.0 times mole, more preferably 1.0 to 3.0 times mole, further preferably 1.0 to 2.0 times mole, per number of mole of the drug.

The pressure-sensitive adhesive layer of the present invention may further contain tackifying resins, plasticizers, fillers, solubilizing agents, stabilizing agents, etc.

The tackifying resin is used to enhance the pressure-sensitive adhesiveness of the pressure-sensitive adhesive layer. The tackifying resin usable is not limited, and can be suitably selected from the known tackifying resins. Specific examples include alicyclic saturated hydrocarbon resins, hydrogenated rosin glycerol esters, aliphatic hydrocarbon resins, terpene resins, and the like. It is preferable that the content of tackifying resin be 40% by mass or less based on the total mass of the pressure-sensitive adhesive layer.

The plasticizer is used to adjust the pressure-sensitive adhesive properties of the pressure-sensitive adhesive layer, the flow properties in the production of the pressure-sensitive adhesive layer and the transdermal absorbability of the drug. When a plasticizer is added, the cohesive force of adhesive layer is reduced and flexible characteristic is imparted. The plasticizer usable is not particularly limited and can suitably be selected from the known plasticizers or softeners. Specific examples include liquid paraffins, liquefied polybutene, liquefied polyisoprene, castor oil, cotton seed oil, palm oil, coconut oil, and the like. It is preferable that the content of plasticizer be 40% by mass or less based on the total mass of the pressure-sensitive adhesive layer.

The filler can be mainly used to adjust the pressure-sensitive adhesive properties of the pressure-sensitive adhesive layer and to block the light. When a filler is used, the pressure-sensitive adhesive force is suppressed. The filler usable is not particularly limited and can suitably be selected from the known fillers. Specific examples include metal oxides such as zinc oxide and titanium oxide, metal hydroxides such as aluminum hydroxide, silicate compounds, calcium carbonate, and the like. It is preferable that the content of the filler be 10% by mass or less based on the total mass of the pressure-sensitive adhesive layer, so that the filler does not inhibit the crosslink of the pressure-sensitive adhesive layer.

The solubilizing agent has an action of enhancing the drug transdermal absorbability by enhancing the drug solubility in the pressure-sensitive adhesive layer. When a solubilizing agent is added, the cohesive force of the pressure-sensitive adhesive layer may sometimes be reduced. The solubilizing agent usable is not particularly limited and can be suitably selected from the known solubilizing agents according to the drug.

The stabilizing agent can be used to enhance the stability of the pressure-sensitive adhesive layer or the drug. The stabilizing agent is not particularly limited and the known antioxidants, ultraviolet absorbers, metal chlorides, and the like, can suitably be used and specific examples include ascorbic acid derivatives, tocopherol derivatives, dibutylhydroxytoluene, edetate, 4-tert-butyl-4'-methoxydibenzoylmethane, calcium chloride, magnesium chloride, and the like. The content of the stabilizing agent is preferably 0.1 to 10.0% by mass, more preferably 0.1 to 5.0% by mass, based on the total mass of the pressure-sensitive adhesive layer.

The backing, on which the pressure-sensitive adhesive layer containing the components described above is formed, is a sheet-like material which physically supports the pressure-sensitive adhesive layer and protects the pressure-sensitive adhesive layer from external environment. It is preferable that the backing be those into which the components in the pressure-sensitive adhesive layer do not permeate or break when the patch is peeled off from the skin. For the backing, elastic or non-elastic films, woven fabrics or non-woven fabrics, porous sheets, sheets of paper or laminates or complexes thereof are used, with films being most preferred. It is preferable that the backing material be those which do not affect the release of drug, and usable are polyesters such as polyethylene terephthalate and polybutylene terephthalate; polyolefines such as polyethylene and polypropylene; nylon; rayon; polyurethane; metal foils such as aluminum; and the like. Polyesters are most desirable since they have flexibility to the skin movement and hardly allow the drug to permeate therethrough.

It is preferable that the thickness of the pressure-sensitive adhesive layer formed on the backing be 20 to 200 μm. Within the above range, sufficient cohesive force for firmness and good pressure-sensitive adhesiveness to the skin can be achieved.

The patch, to protect the pressure-sensitive adhesive layer while stored, or the like, may be those provided with a release liner on the pressure-sensitive adhesive layer. When the patch is to be applied, the release liner is peeled off. For the release liner, films, sheets of paper or laminates or complexes thereof are used without particular limitation, and films are most desirable. For the release liner material, polyesters such as polyethylene terephthalate, polybutylene terephthalate and polyethylene naphthalate; polyolefines such as polyethylene and polypropylene; nylon; metal foils such as aluminum; and the like, are used, with polyesters being most desirable in the light of stability over time. It is preferable that the release liner be surface-treated with mold release treatment such as siliconization, or the like, for easy peeling.

The patch is typically packed, and the packaging container usable is an aluminum laminate package composed of multilayer film laminate with the sealant layer being polyacrylonitrile, and when a deoxidizer is included in the packaging container, the drug stability can further be improved.

The patch can be produced by conventional methods such as solvent method and hot melt method. For example, when the patch is produced by the solvent method, other components are added to an organic solvent solution of the pressure-sensitive adhesive base to be added and stirred, the solution is spread over the backing and dried to form a pressure-sensitive adhesive layer, whereby the patch is obtained. Alternatively, when the pressure-sensitive adhesive base to be added can be coated by the hot melt method, the pressure-sensitive adhesive base is dissolved at a high temperature, other components are added thereto and stirred, and the solution is spread over the backing to form a pressure-sensitive adhesive layer, whereby the patch of the present invention is obtained. Additionally, the patch of the present invention can also be obtained by forming the pressure-sensitive adhesive layer using a release liner in place of the backing, followed by laminating the backing thereto.

EXAMPLES

Hereinafter, the present invention is specifically described with reference to Reference Examples, Examples and Comparative Example, but is not limited thereto.

<Production of Patch>

Reference Examples 1-3

According to the formulation (% by mass) shown in Table 1, tamsulosin hydrochloride, sodium acetate and fatty acid ester and each of acrylate polymers 1 to 3 were mixed and the mixtures were stirred to obtain homogeneously dissolved products. These dissolved products were spread over sheets of release paper, the solvent was dried and removed and the sheets of release paper were laminated to polyethylene terephthalate (PET) film backing to obtain the patches of Reference Examples 1 to 3. In Table 1, the acrylate polymer 1 is an acrylate polymer which has a hydroxyl group and contains a crosslinking agent. The acrylate polymer 2 is an acrylate polymer which has a carboxyl group and contains a crosslinking agent. The acrylate polymer 3 is an acrylate polymer which does not have a hydroxyl group or a carboxyl group or contain a crosslinking agent.

<Drug Permeation Test>

Reference Examples 1 to 3

The patches of Reference Examples 1 to 3 were evaluated for the drug permeability by the following method. The ventral skin of a hairless mouse was peeled and mounted, with the dermis side facing a receptor liquid, on a flow through cell in which warm water of 37° C. was circulated around the outer periphery. Subsequently, the patch having an application area of 5 cm$^2$ was applied on the corneum side of the skin, and, using phosphate buffer solution (PBS) as a receptor liquid, the receptor liquid was sampled hourly up to 24 hours. While measuring the flow rate of the sampled solutions, the drug concentrations were measured using high speed liquid chromatography. Based on the obtained measured values, the drug permeation rate per hour was calculated, whereby the maximum value thereof. Jmax (µg/cm$^2$/hr) and the accumulative permeation amount (µg) over the period of 24 hours were determined. The results are shown in Table 1.

TABLE 1

|   | Tamsulosin hydrochloride | Sodium acetate | Fatty acid ester | Acrylate polymer 1 | Acrylate polymer 2 | Acrylate polymer 3 | Hairless mouse skin permeability Jmax (µg/cm$^2$/hr) | Accumulative permeation amount (µg) |
|---|---|---|---|---|---|---|---|---|
| Reference Example 1 | 5.0% | 1.4% | 8.6% | 85.0% | — | — | 2.81 | 30.44 |
| Reference Example 2 | 5.0% | 1.4% | 8.6% | — | 85.0% | — | 0.00 | 0.00 |
| Reference Example 3 | 5.0% | 1.4% | 8.6% | — | — | 85.0% | 0.40 | 3.68 |

The patch of Reference Example 1 containing the acrylate polymer 1 having a hydroxyl group exhibited better drug permeability than the patches of Reference Examples 2 and 3 respectively containing the acrylate polymers 2 and 3 having no hydroxyl group.

<Production of Patch>

Examples 1 to 6

According to the formulation (% by mass) shown in Table 2, tamsulosin hydrochloride, sodium acetate, polyvinylpyrrolidone and fatty acid ester were mixed thoroughly in the solvent and the mixtures were mixed with the acrylate polymer having a hydroxyl group in which aluminum chloride was dissolved and stirred to obtain the homogeneously dissolved products. These dissolved products were spread over sheets of release paper, the solvent was dried and removed and the sheets of release paper were laminated to polyethylene terephthalate (PET) film backing, thereby obtaining the patches of the present invention.

Comparative Example 1

A patch was produced according to the formulation shown in Table 2 in the same manner as in Examples 1 to 6 except that aluminum chloride was not used.

<Measurement Method of pH>

The preparation (5 cm$^2$) from which a sheet of release paper was peeled off was immersed in 20 mL of distilled water, which was stirred for 24 hours, and the pH of test solution was measured.

TABLE 2

|  | Tamsulosin hydrochloride | Sodium acetate | Acrylate polymer having hydroxyl group | Polyvinyl-pyrrolidone | Fatty acid ester | Aluminum chloride | pH |
|---|---|---|---|---|---|---|---|
| Example 1 | 5.0% | 1.4% | 83.5% | 5.0% | 5.0% | 0.1% | — |
| Example 2 | 5.0% | 1.4% | 83.4% | 5.0% | 5.0% | 0.2% | — |
| Example 3 | 5.0% | 1.4% | 83.3% | 5.0% | 5.0% | 0.3% | — |
| Example 4 | 5.0% | 1.4% | 83.2% | 5.0% | 5.0% | 0.4% | — |
| Example 5 | 5.0% | 1.4% | 83.1% | 5.0% | 5.0% | 0.5% | 7.97 |
| Example 6 | 5.0% | 1.4% | 82.6% | 5.0% | 5.0% | 1.0% | 4.84 |
| Comparative Example 1 | 5.0% | 1.4% | 83.6% | 5.0% | 5.0% | — | 8.49 |

<Drug Content Stability Test>

The drug content stabilities of the patches prepared in Examples 1 to 5 and Comparative Example 1 were evaluated by the method below.

(Storage)

The produced patches were cut to size 10 cm² to obtain a sample for the test. Each sample was hermitically sealed in an aluminum package and stored in a temperature/humidity controlled chamber maintained at 60° C. or 40° C. at a humidity of 75% for 2 weeks, 1 month or 3 months.

(Measurement)

The residual drug in each patch was extracted in the following manner and the residual amount after storage with respect to the initial content was calculated against the initial value (%). The PET film was peeled off from the patch which had been stored and the patch was placed in a glass centrifuge tube (50 mL volume). Subsequently, 10 ml of tetrahydrofran was added as an extraction liquid and the tube was shaken for 1 hour. Subsequently, a suitable internal standard substance was added, methanol was further added to give the total amount of 50 ml and the tube was shaken for 1 hour. Each of the prepared test samples was analyzed by high speed liquid chromatography and the drug contained was determined. The values of drug content of each sample ($N_i$) and the drug content of the initial sample before storage ($N_o$) were substituted into the relational equation shown in the following formula (I) to obtain the value against the initial value ($R_i$), which is shown in Table 3.

Value against initial value $R_i$ (%)=$N_i/N_o$×100  (1)

In Table 3, for example, "60° C.-2W" represents the storage conditions: at 60° C. for 2 weeks, and "40° C.-1M" represents the storage conditions: at 40° C. for 1 month.

TABLE 3

|  | 60° C.-2W | 60° C.-1M | 40° C.-1M | 40° C.-3M |
|---|---|---|---|---|
| Example 1 | 96.9 | 95.4 | 100.2 | 96.4 |
| Example 2 | 97.4 | 97.0 | 100.1 | 97.1 |
| Example 3 | 99.0 | 95.4 | 99.3 | 95.3 |
| Example 4 | 97.6 | 97.1 | 99.2 | 97.3 |
| Example 5 | 99.2 | 97.2 | 100.1 | 97.1 |
| Comparative Example 1 | 94.8 | 91.5 | 97.2 | 95.3 |

The patches of Examples 1 to 5 retained a high drug content stability even after stored for an extended period of time.

<Drug Permeation Test>

Examples 1 to 6 and Comparative Example 1

The patches of Examples 1 to 6 and Comparative Example 1 were evaluated for the drug permeability by the following method. The ventral skin of a hairless mouse was peeled and mounted, with the dermis side facing a receptor liquid, on a flow through cell in which warm water of 37° C. was circulated around the outer periphery. Subsequently, the patch having an application area of 5 cm² was applied on the corneum side of the skin, and using phosphate buffer solution (PBS) as a receptor liquid, the receptor liquid was sampled hourly up to 24 hours. While measuring the flow rate of the sampled solution, the drug concentration was measured using high speed liquid chromatography. Based on the obtained measured values, the drug permeation rate per hour was calculated, whereby the maximum value thereof. Jmax (μg/cm²/hr) was determined. The results are shown in FIG. 1.

The patches of Examples 1 to 3 and Comparative Example 1 exhibited good drug permeability. The patch of Example 6 exhibited substantially no drug permeability, however, this is presumably caused by the reduced pH of the pressure-sensitive adhesive layer by the addition of aluminum chloride and thus tamsulosin, a basic drug, hardly permeates.

INDUSTRIAL APPLICABILITY

The patch of the present invention has good drug content stability over an extended period of time and is useful in the medical industry aiming at prevention and treatment of diseases.

The invention claimed is:

1. A patch comprising a backing and a pressure-sensitive adhesive layer on the backing, wherein the pressure-sensitive adhesive layer contains a pressure-sensitive adhesive base composed of a vinyl polymer having a hydroxyl group, a drug, polyvinylpyrrolidone and aluminum chloride wherein a content of aluminum chloride is 0.1 to 5.0% by mass based on the total mass of the pressure-sensitive adhesive layer, and wherein the pressure-sensitive adhesive base has a higher drug content stability than the same pressure-sensitive adhesive base not containing aluminum chloride.

2. The patch according to claim 1, wherein the drug is at least one selected from the group consisting of basic drugs and pharmaceutically acceptable salts thereof.

3. The patch according to claim 1, wherein the drug is at least one selected from the group consisting of tamsulosin and pharmaceutically acceptable salts thereof.

4. The patch according to claim 1, wherein a content of the polyvinylpyrrolidone is 1 to 20% by mass based on the total mass of the pressure-sensitive adhesive layer.

5. The patch according to claim 1, wherein a ratio by mass of the multivalent metal chloride to the drug is 1:100 to 2:1.

* * * * *